United States Patent
Komatsu et al.

(10) Patent No.: US 10,145,094 B2
(45) Date of Patent: Dec. 4, 2018

(54) SANITARY APPARATUS WITH A HOT AIR BLOWER EQUIPPED WITH AN ION GENERATING DEVICE FOR DISINFECTION, DEODORIZATION, OR THE LIKE

(71) Applicant: Lixil Corporation, Tokyo (JP)

(72) Inventors: Toshihiko Komatsu, Tokyo (JP); Hiroaki Watanabe, Tokyo (JP); Yasuyuki Furutani, Tokyo (JP)

(73) Assignee: Lixil Corporation, Tokyo (JP)

( * ) Notice: Subject to any disclaimer, the term of this patent is extended or adjusted under 35 U.S.C. 154(b) by 0 days.

(21) Appl. No.: 15/496,016

(22) Filed: Apr. 25, 2017

(65) Prior Publication Data
US 2017/0314247 A1 Nov. 2, 2017

(30) Foreign Application Priority Data
Apr. 28, 2016 (JP) ................ 2016-091521

(51) Int. Cl.
| | | |
|---|---|---|
| *E03D 9/00* | (2006.01) | |
| *A61L 2/14* | (2006.01) | |
| *A61L 2/26* | (2006.01) | |
| *A61L 9/22* | (2006.01) | |
| *E03D 9/08* | (2006.01) | |

(52) U.S. Cl.
CPC ............... *E03D 9/005* (2013.01); *A61L 2/14* (2013.01); *A61L 2/26* (2013.01); *A61L 9/22* (2013.01); *A61L 2202/11* (2013.01); *A61L 2202/15* (2013.01); *E03D 9/08* (2013.01)

(58) Field of Classification Search
CPC ... E03D 9/05; E03D 9/005; A61L 2/14; A61L 2/26; A61L 2202/11; A61L 2202/15

USPC ................ 4/348, 347, 453, 352
See application file for complete search history.

(56) References Cited

U.S. PATENT DOCUMENTS

| | | | | |
|---|---|---|---|---|
| 3,486,173 A * | 12/1969 | Youngblood | .......... | A61G 9/003 4/453 |
| 3,763,505 A * | 10/1973 | Zimmerman | .......... | E03D 9/052 4/213 |
| 4,200,940 A * | 5/1980 | Buchanan | ............ | A47K 13/307 4/213 |
| 6,351,855 B1 * | 3/2002 | Allen | ........................ | E03D 9/05 4/213 |
| 6,640,049 B1 * | 10/2003 | Lee | ........................ | A45D 20/08 34/96 |
| 8,709,137 B2 * | 4/2014 | Chan | ........................ | A61L 2/022 4/306 |

(Continued)

FOREIGN PATENT DOCUMENTS

JP 2015158103 A 9/2015

*Primary Examiner* — Benjamin R Shaw
(74) *Attorney, Agent, or Firm* — Wood Herron & Evans LLP (57) ABSTRACT

A sanitary apparatus includes: a fan; an air-blowing passage provided on a downstream side from the fan and includes a first air-blowing passage and a second air-blowing passage partitioned from each other; a heater for heating air of the first air-blowing passage; and an ion generating device generating ions to be carried by the air blowing of the second air-blowing passage, in which the ion generating device is installed on a downstream side from the heater so that the generated ions join the air blown from the first air-blowing passage by the air blowing of the second air-blowing passage.

8 Claims, 9 Drawing Sheets

(56) References Cited

U.S. PATENT DOCUMENTS

| | | | |
|---|---|---|---|
| 2006/0064805 A1* | 3/2006 | Yamamoto | E03D 9/05 4/213 |
| 2008/0060119 A1* | 3/2008 | Pinizzotto | A47K 13/302 4/217 |
| 2009/0158515 A1* | 6/2009 | Bruno | E03D 9/052 4/348 |
| 2011/0047689 A1* | 3/2011 | Gianelloni | E03D 9/052 4/348 |
| 2012/0054950 A1* | 3/2012 | Abunameh | E03D 9/05 4/348 |

* cited by examiner

FIG. 10

SANITARY APPARATUS WITH A HOT AIR BLOWER EQUIPPED WITH AN ION GENERATING DEVICE FOR DISINFECTION, DEODORIZATION, OR THE LIKE

BACKGROUND OF THE INVENTION

Field of the Invention

The present invention relates to a sanitary apparatus in which a hot air blower with an ion generating device discharging ions in air is provided at a toilet bowl body. Priority is claimed on Japanese Patent Application No. 2016-091521, filed on Apr. 28, 2016, the content of which is incorporated herein by reference.

Description of Related Art

In the related art of a sanitary apparatus which is used in a flushing type toilet, sanitary devices that include a hot air blower installed for drying a local portion with warm air after washing with warm water are suggested. In recent years, as the hot air blower, a hot air blower equipped with an ion generating device, in which an ion generating device generating ions is added to the hot air blower and blows air for disinfection, deodorization, or the like. have been suggested.

For example, in a sanitary washing device described in Japanese Unexamined Patent Application, First Publication No. 2015-158103, as a portion of a function portion installed in a toilet bowl body, a heater for heating air and an electrostatic atomization device for generating ions are stacked vertically in the vicinity of an opening of a blower fan, and an blowout port is installed in front of the blower fan. In addition, a shutter is provided at the blowout port. The shutter is fully opened at the time of driving the heater, and at the time of driving the electrostatic atomization device, the shutter is half-opened.

SUMMARY OF THE INVENTION

However, in the sanitary washing device described in the above-mentioned Japanese Unexamined Patent Application, First Publication No. 2015-158103, since the heater and the electrostatic atomization device are installed in parallel in its entirety, there is a concern that an operation of the electrostatic atomization device may be affected by heat of the heater. In addition, since the heater and the electrostatic atomizationg device are arranged in parallel in a direction orthogonal to a blowing direction of the fan, an air volume is dispersed. In addition, since the electrostatic atomization device is provided in the vicinity of the fan, a distance to the blowout port becomes long, a part of the generated ions disappears before being discharged from the blowout port, and there is a disadvantage in that the amount of the ions discharged from the blowout port is small.

The present invention is made in consideration of the above-described circumstances and an object thereof is to provide a sanitary apparatus in which an ion generating device is prevented from being affected from heat of a heater and many ions is capable of being discharged from a blowout port to the outside.

SUMMARY OF THE INVENTION

According to an aspect of the present invention, a sanitary apparatus including: a fan for blowing air; an air-blowing passage which is provided on a downstream side from the fan and includes a first air-blowing passage and a second air-blowing passage which are partitioned from each other; a heater for heating air in the first air-blowing passage; and an ion generating device generating ions to be carried by the air blowing of the second air-blowing passage, wherein the ion generating device is installed on a downstream side from the heater so that the generated ions join the air blown from the first air-blowing passage by the air blowing of the second air-blowing passage.

According to the present invention, since the ion generating device is installed on the downstream side from the heater, the ion generating device is possible to generate ions without being affected by the heat of the heater. In addition, since the ion generating device is installed close to the blowout port, the ions to be generated allow joining the air blown from the first air-blowing passage, thereby the sanitary apparatus is possible to efficiently blow the ions to the outside.

The sanitary apparatus according to the present invention may further include a partition wall which faces the first air-blowing passage between the first air-blowing passage and the second air-blowing passage, wherein the partition wall is inclined gradually close to the first air-blowing passage side toward the downstream side of the air blowing.

According to the present invention, since the partition wall of the second air-blowing passage is inclined gradually close to the first air-blowing passage side toward the downstream side of the air blowing, the warm air of the first air-blowing passage is difficult to hit the ion generating device, and the ion generating device is possible to stably generate ions.

In the sanitary apparatus according to the present invention, the second air-blowing passage may be inclined gradually close to the first air-blowing passage side toward the downstream side of the air blowing.

According to the present invention, since the second air-blowing passage may be inclined gradually close to the first air-blowing passage side toward the downstream side of the air blowing, the sanitary apparatus is possible to join ions with the air blown from the first air-blowing passage. The second air-blowing passage may have a tapered shape widening on the downstream side or may be an approximately parallel flow passage.

In the sanitary apparatus according to the present invention, an upper guide portion and a lower guide portion may be provided in the vicinity of a blowout port of the air-blowing passage in which the air blowing of the first air-blowing passage and the air blowing of the second air-blowing passage join with each other, and the upper guide portion and the lower guide portion may be formed such that the air blowing in the blowout port is directed upward by the upper guide portion and the lower guide portion.

According to the present invention, the sanitary apparatus is possible to discharge air including ions toward a local portion of a user by blowing the air including ions upward from the blowout port.

In the sanitary apparatus according to the present invention, a temperature measuring device measuring a temperature of the air may be installed in the air-blowing passage on the downstream side from the first air-blowing passage, and wherein the temperature measuring device may be installed at a position where is further separated from the center in a width direction of the air-blowing passage than the ion generating device.

According to the present invention, since the temperature measuring device is apart from the ion generating device and the heater, the temperature measuring device is possible to decrease the influence of high-voltage discharge for generating ions and the heat by the heater.

The sanitary apparatus according to the present invention may further include a duct case covering the air-blowing passage and blowing out ions to be generated with the high-pressure discharge by an ion generating unit of the ion generating device from the blowout port of the air-blowing passage, wherein a linear distance between the ion generating unit of the ion generating device and the blowout port may be set to a predetermined distance, and an electric-conductive distance may be set to be longer than the predetermined distance by that a transmission path along a wall surface of the duct case between the ion generating unit and the blowout port which passes through a bypass portion in which the electric conduction is bypassed.

According to the present invention, since an electric-conductive distance is set to be longer than the predetermined distance by that a transmission path along a wall surface of the duct case between the ion generating unit and the blowout port which passes through a bypass portion in which the electric conduction is bypassed, the sanitary apparatus is possible to prevent electricity from flowing to an user who comes into contact with the blowout port, and it is possible to secure safety. In addition, since the linear distance between the ion generating unit of the ion generating device and the blowout port is set to a predetermined distance, the sanitary apparatus is capable of downsizing and the sanitary apparatus is capable of flow out large amount of ions by installing the ion generating device closer to the blowout port.

The sanitary apparatus according to the present invention may further include: a toilet bowl body; and a cover which covers the ion generating device, wherein the ion generating device may be installed at a position inside and adjacent to a front cover portion of the cover, the front cover facing the toilet bowl body.

According to the present invention, since the ion generating device is installed at a position inside and adjacent to the front cover portion of the cover, the ion generating device is possible to install at a position closer to the blowout port, and the sanitary apparatus is possible to effectively discharge the generated ions through a short flow passage.

According to the sanitary apparatus of the present invention, since the ion generating device is installed away from the downstream side from the heater, the ion generating device is capable of being prevented from being affected by heat of the heater, and many generated ions are possible to effectively discharge to the outside from the blowout port.

DETAILED DESCRIPTION OF THE INVENTION

Hereinafter, a flushing type toilet bawl according to an embodiment of the present invention will be described with reference to the accompanying drawings.

FIGS. 1 to 6 are views showing a flushing type toilet bawl 1 according to the embodiment of the present invention. In the flushing type toilet bawl 1 of the embodiment shown in FIG. 1, a toilet seat 3 is installed on an upper surface of a toilet bowl body 2 made of pottery, and a cover 5 in which a function portion 4 is accommodated is installed at the rear of the toilet seat 3. The function portion 4 includes a local washing nozzle 9, a hot air blower 10, or the like. Hereinafter, the function portion 4 including the hot air blower 10 with an ion generating device 11 and the cover 5 covering the function portion 4 are referred to as a sanitary apparatus 6.

For example, the ion generating device 11 includes various type devices which generates ions for disinfection or deodorization in air such as a device generating ions by plasma discharge to suppresses the action of viruses floating in air, and to decompose and remove floating mold bacteria or the like in the air, or an electrostatic atomization device.

Figure 2:
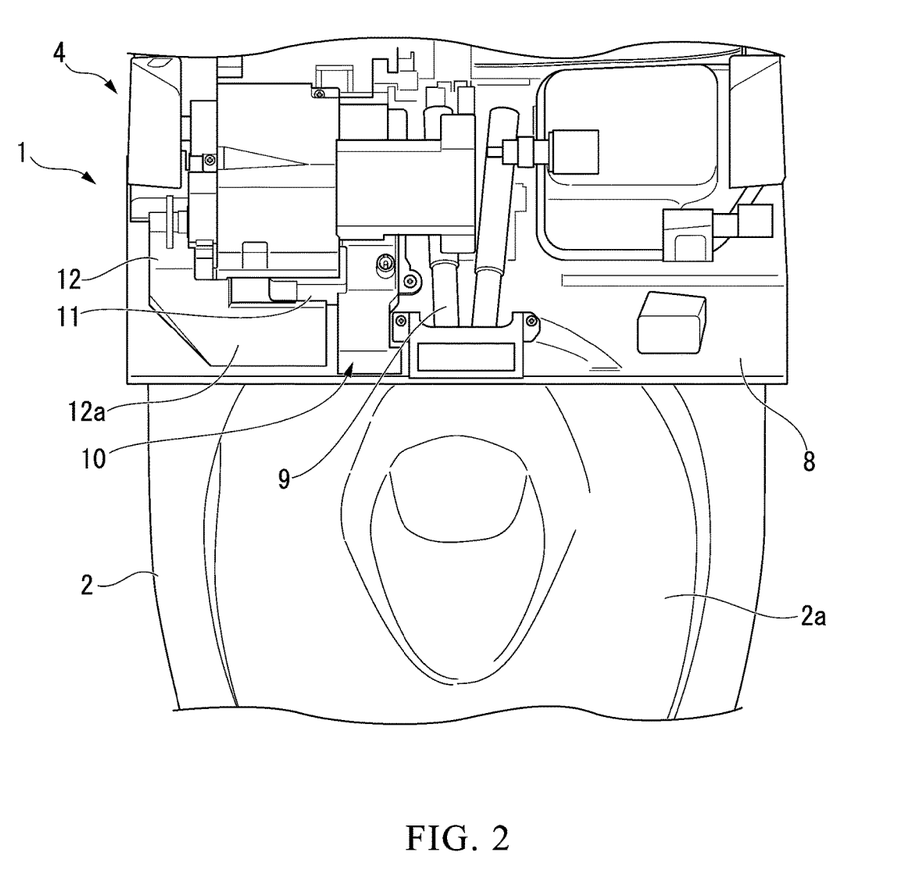
FIG. 2 is a perspective view of a main portion in a state where a cover of a function portion shown in FIG. 1 is removed.

FIG. 2 is a view showing the function portion 4 installed on the toilet bowl body 2 in a state where the cover 5 is removed. The function portion 4 is installed on a base plate 8 installed on the upper portion of the toilet bowl body 2. The local washing nozzle 9 is installed in the center of the front portion and where is faced the bowl portion (toilet bowl) 2a of the toilet bowl body 2 of the function portion 4. A hot air blower 10 blowing warm air is installed at a position adjacent to the local washing nozzle 9. The ion generating device 11 is mounted on the hot air blower 10.

A deodorizing device 12 is installed next to the hot air blower 10, and a deodorizing suction duct 12a of the deodorizing device 12 is installed on the front side of the ion generating device 11. A distal end of the local washing nozzle 9 and a blowout port 18 of the hot air blower 10 are installed on the lower surface of a front end portion of the base plate 8, and a suction port of the deodorizing suction duct 12a is installed at a position adjacent to the distal end of the local washing nozzle 9 and the blowout port 18.

Figure 3:
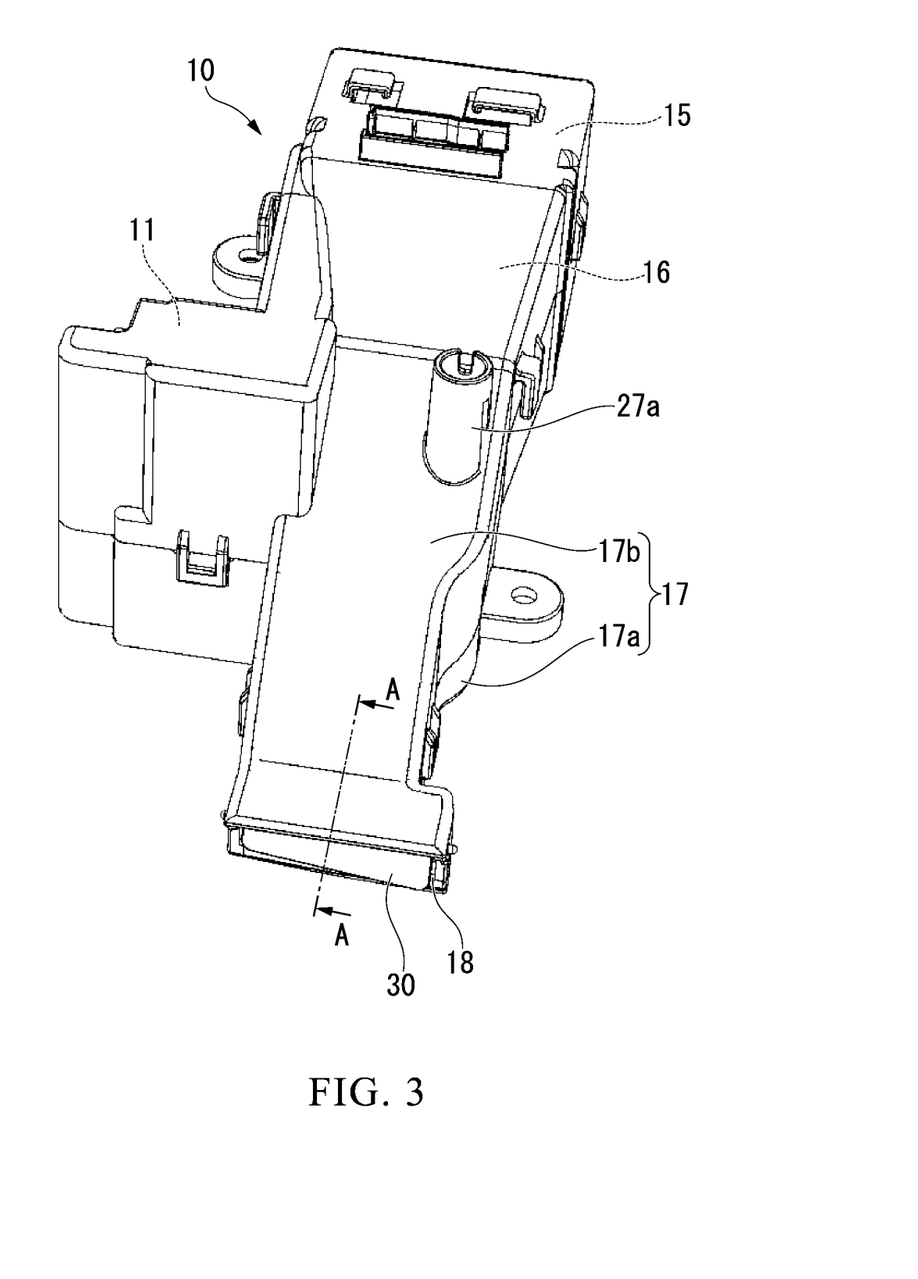
FIG. 3 is a perspective view of the air blower with the ion generating device shown in FIG. 2.
Figure 4:
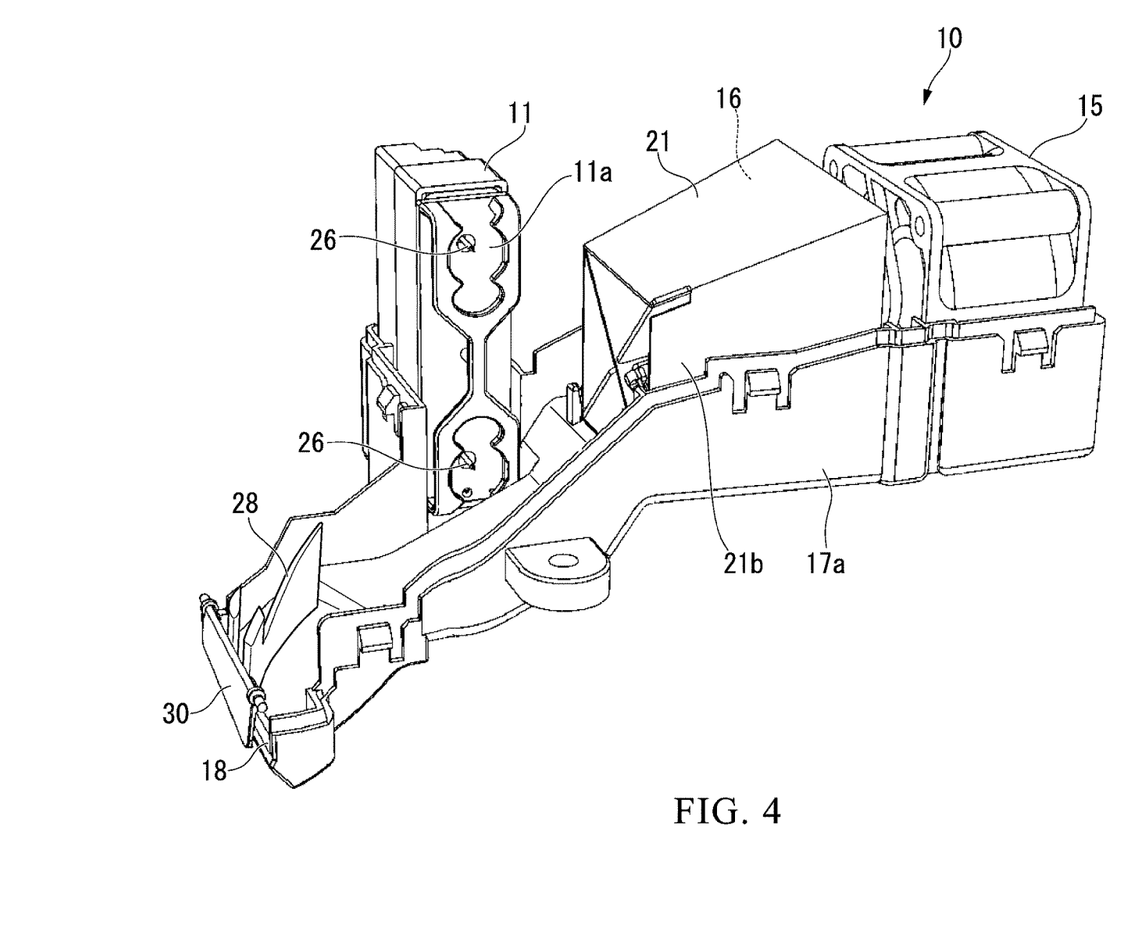
FIG. 4 is a perspective view in a state where an upper duct case of the air blower with the ion generating device shown in FIG. 3 is removed.
Figure 5:
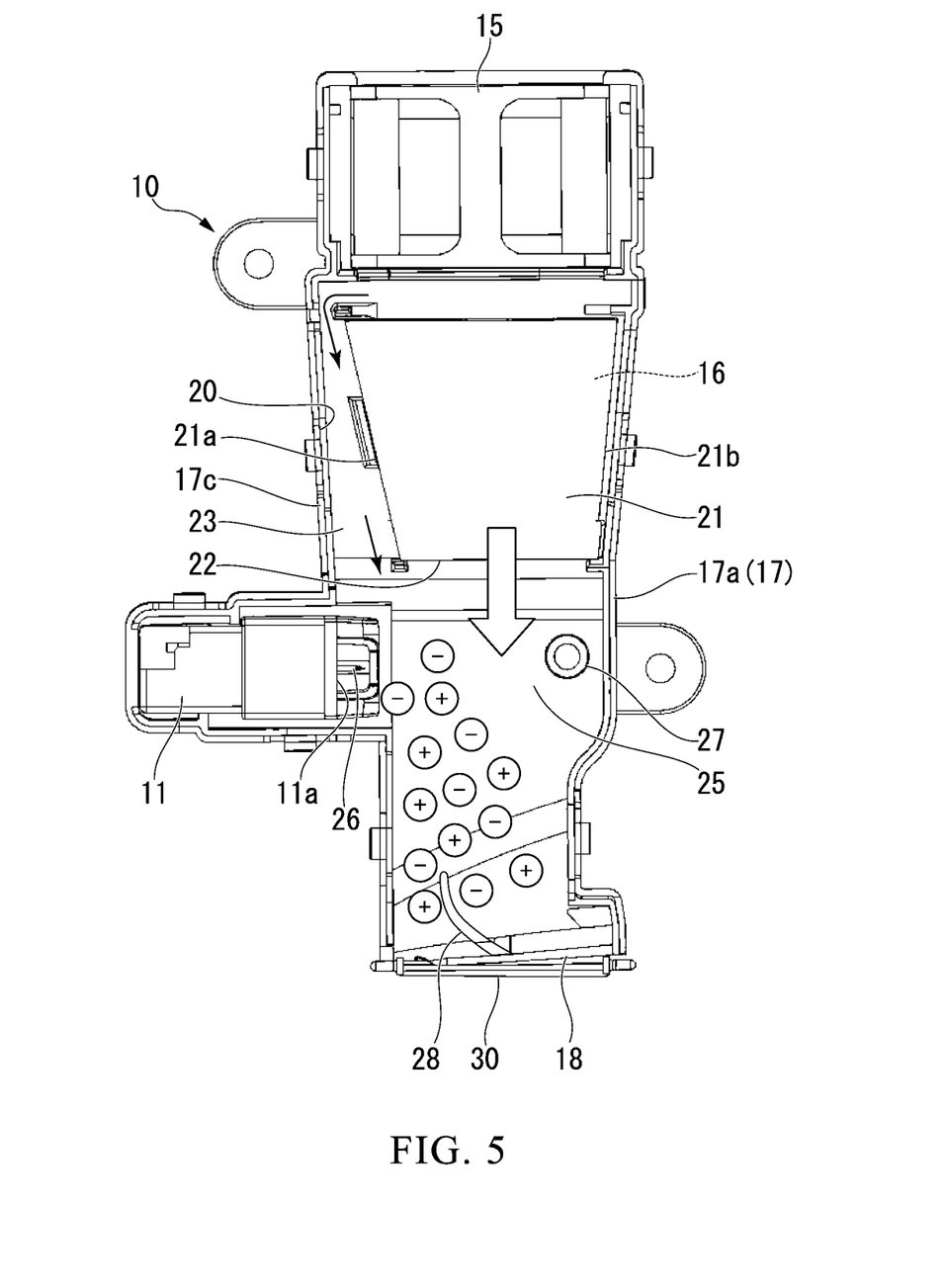
FIG. 5 is a plan view of the air blower with the ion generating device shown in FIG. 4.

FIGS. 3 to 5 are views showing the hot air blower 10 with the ion generating device 11. A heater 16 and the ion generating device 11 are installed in the hot air blower 10 with the ion generating device 11. The heater 16 is installed in front of a fan 15. The ion generating device 11 is installed at a side portion in front of the heater 16 so as to protrude outward from the side portion of the heater 16. For example, the heater 16 is formed by winding a nichrome wire or the like in a coil shape.

The fan 15, the heater 16, and the ion generating device 11 are placed in a lower duct case 17a and covered with an upper duct case 17b. The duct case 17 is formed in an approximately tubular shape by fitting the upper duct case 17b into the lower duct case 17a. The blowout port 18 for discharging warm air, ions, or the like is formed at a distal end portion facing the bowl portion 2a of the toilet bowl body 2 of the duct case 17.

In a plan view of the hot air blower 10 with the ion generating device 11 shown in FIG. 5, an air-blowing passage 20 of the fan 15 is formed by the duct case 17 in front of the fan 15. For example, a rectangular tubular air-blowing tubular body 21, in which the heater 16 is accommodated, is installed in a portion of the air-blowing passage 20. The air-blowing tubular body 21 is formed in a tapered shape in which both side surfaces 21a and 21b and the upper and lower side surfaces are close to each other from a rear opening on the fan 15 side toward a front end opening on the blowout port 18 side.

The side surface 21a of the air-blowing tubular body 21 on the ion generating device 11 side is gradually inclined so as to be separated from a left wall 17c of the duct case 17 in FIG. 5 from a rear end side toward a front end side of the air-blowing tubular body 21. The air-blowing tubular body 21 forms a first air-blowing passage 22. In the first air-blowing passage 22, most of air sent from the fan 15 is heated by the heater 16 so as to be blown as warm air. In addition, since the air-blowing tubular body 21 has a tapered front end opening which narrows toward the front end side, an air-blowing speed becomes high at the outlet side. The first air-blowing passage 22 forms a main flow passage in which a large amount of air flows as a main flow.

The side surface 21a is inclined in a plan view. As the result, in the air-blowing passage 20, a flow passage between the side surface 21a of the air-blowing tubular body 21 and the side wall 17c of the duct case 17 is formed in a tapered shape in which a space between the side surface 21 and the side wall 17c of the duct case 17 is wide on the rear end and is narrow on the front end side. The flow passage between the side surface 21a and the side wall 17c constitutes a second air-blowing passage 23. The second air-blowing passage 23 is capable of blowing a portion of air sent from the fan 15 as an auxiliary flow. The second air-blowing passage 23 forms an auxiliary flow passage through which a relatively small amount of air flows.

Therefore, in the air-blowing passage 20 formed by the duct case 17, the first air-blowing passage 22 and the second air-blowing passage 23 are arranged in parallel. In addition, the first air-blowing passage 22 and the second air-blowing passage 23 join with each other in front of the heater 16. The ion generating device 11 is installed outside a junction portion 25. A distal end surface 11a of the ion generating device 11 is disposed on approximately an extension line of the side wall 17c of the second air-blowing passage 23. A pair of needle-like ion electrodes 26 which protrudes from the distal end surface 11a is ion generating units, and the ion electrodes 26 are disposed on an extension line of the second air-blowing passage 23.

Since the second air-blowing passage 23 gradually becomes wider from the rear end side toward the distal end side thereof by an inclination of the side surface 21a, the air blowing is diffused. In addition, since the ion electrodes 26 are disposed on the extension line of the second air-blowing passage 23, ions generated in the ion electrodes 26 allows to be diffused into the junction portion 25 by the auxiliary flow. In the present embodiment, the pair of ion electrodes 26 is attached on the upper portion and the lower portion of the distal end surface 11a. However, the number of the ion electrodes 26 to be attached is not limited to two but also any number is capable of being selected.

For example, as a temperature measuring device, a thermistor 27 is attached to the upper duct case 17b at the junction portion 25 where is the downstream sides of the first air-blowing passage 22 and the second air-blowing passage 23 in the air-blowing passage 20. The temperature measuring device is provided for measuring the temperature of the air heated by the heater 16. The thermistor 27 is attached to apart downstream from the heater 16 by a predetermined distance so as not to be affected by the heat of the heater 16.

The ion generating device 11 is installed on a side portion of the thermistor 27. The thermistor 27 is also attached to apart from the ion electrodes 26, which emits high-pressure discharge, by a predetermined distance so as not to be influenced by the operations of the ion electrodes 26. That is, the thermistor 27 is preferably installed at a position further away from the ion generating device 11 than the center in the width direction of the air-blowing passage 20 in the junction portion 25. A tubular portion 27a protrudes from an upper surface of the upper duct case 17b shown in FIG. 3, and elongated vertically down side on the junction portion 25. The tubular portion 27a accommodates and protects the thermistor 27.

For example, the duct case 17 has a shape which is inclined downward between the air-blowing tubular body 21 and the blowout port 18. A guide portion 28 is formed in the vicinity of the blowout port 18. For example, the guide portion 28 has a shape such as a curved plate shape or a flat plate shape. The guide portion 28 is formed so as to guide the air blowing toward the local washing nozzle 9 side, that is, toward the local portion side of a user who sits on the toilet seat 3. As a result, the warm air heated by the heater 16 and the ions generated by the ion generating device 11 are blown to the periphery of the local portion of a user.

Figure 6:
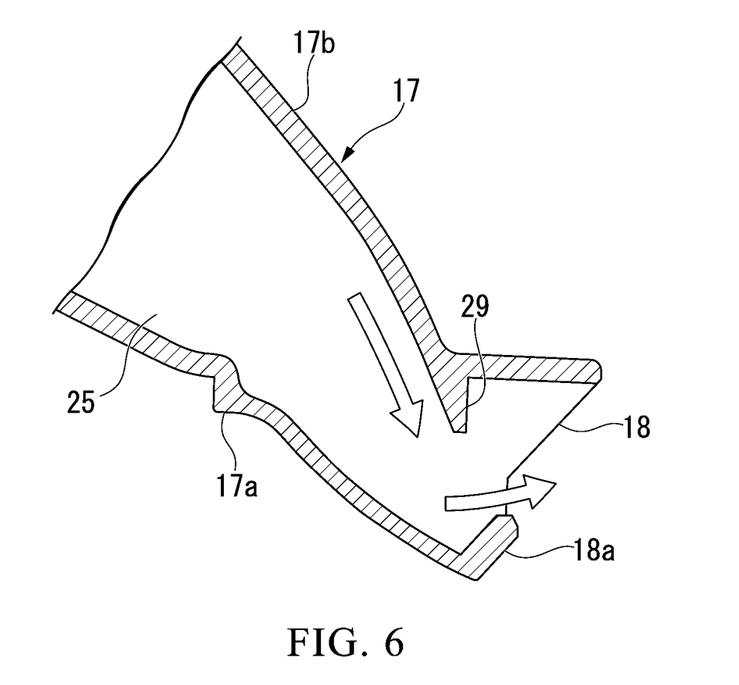
FIG. 6 is a cross sectional view taken along line A-A of a duct case on a blowout port side of the air blower with the ion generating device shown in FIG. 3.

In the longitudinal cross sectional view in the vicinity of the blowout port 18 of the duct case 17 shown in FIG. 6, an upper guide plate 29 is formed downward on an inner surface of an upper part of the upper duct case 17b. A lower guide 18a which covers the lower portion of the blowout port 18 is formed so as to protrude in the blowout port 18. Therefore, the air blown from the junction portion 25 toward the blowout port 18 is sent downward and to the lower guides 18a by the upper guide plate 29, is regulated upward by the lower guide 18a of the blowout port 18 on the downstream side thereof, and is discharged from the blowout port 18.

Although an openable and closable shutter 30 is installed in the blowout port 18, the shutter 30 may be omitted.

Figure 1:
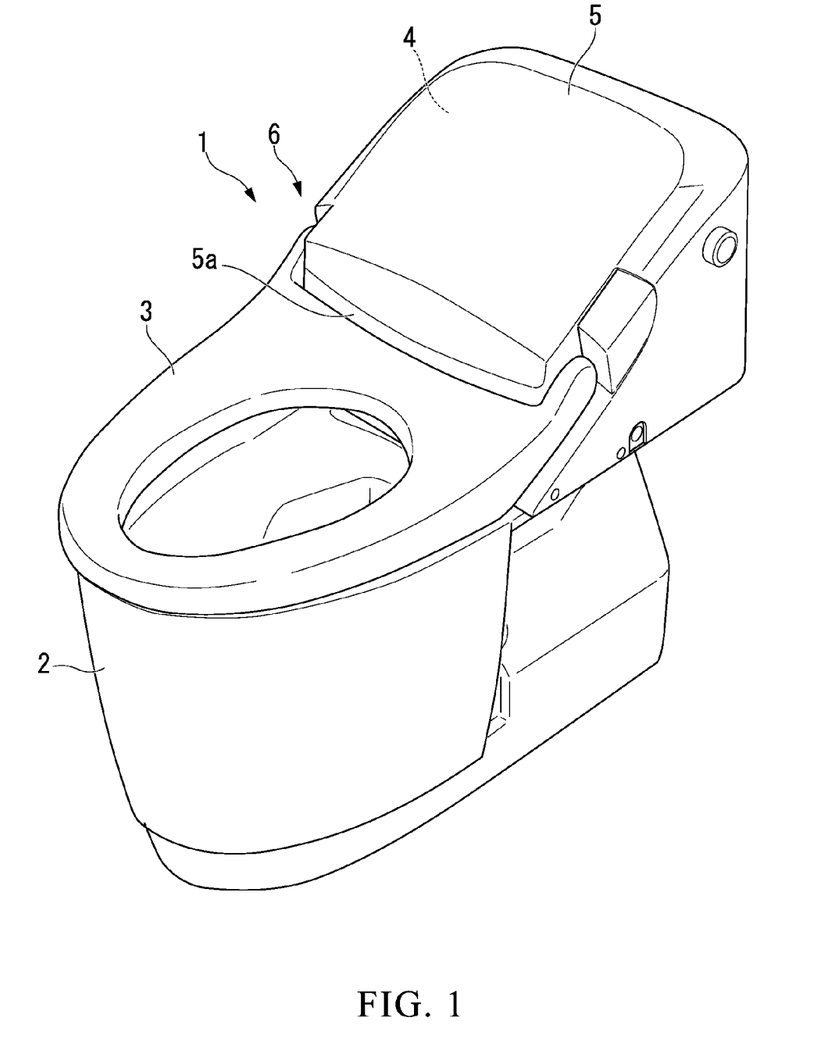
FIG. 1 is a perspective view of a flushing type toilet bawl provided with an air blower with an ion generating device according to an embodiment of the present invention.
Figure 7:
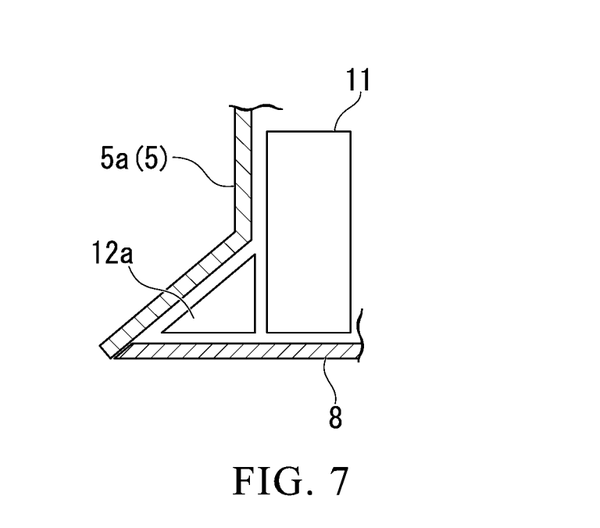
FIG. 7 is a partial cross sectional view of a front cover portion of a cover which covers a deodorizing suction duct and the ion generating device.

As shown in FIGS. 1, 2 and 7, the local washing nozzle 9 or the hot air blower 10 with the ion generating device 11 is mounted at a front end part of the base plate 8 inside a front cover portion 5a of the cover 5 which covers the function portion 4. The front cover portion 5a faces the toilet bowl body 2 or the toilet seat 3. Particularly, as shown in a partial cross sectional view of FIG. 7, the front cover portion 5a covers the deodorizing suction duct 12a of the deodorizing device 12 and the ion generating device 11 which are provided in the vicinity of the inner surface of the front cover portion 5a.

Accordingly, the ion generating device 11 is capable of being installed near the blowout port 18, and is capable of being installed at a position as close to the bowl portion 2a of the toilet bowl body 2 as possible inside the front cover portion 5a of the cover 5 covering the function portion 4. As a result, most of the ions generated by the ion generating device 11 are efficiently discharged from the blowout port 18.

Meanwhile, in the flushing type toilet bawl 1, the pair of upper and lower ion electrodes 26 of the ion generating device 11 discharge high voltage to generate ions. Therefore, a portion of electric current may be transmitted to the blowout port 18 through the duct case 17. However, since there is a possibility that a user, a cleaner, or the like may touch the blowout port 18 with hands, the high-pressure discharge of the ion generating device 11 is necessary to be set such that a portion of current flowing via the duct case 17 is not transmitted to the blowout port 18 for preventing an electric shock.

Therefore, according to the standard set by International Electro-technical Commission (IEC), a shortest electric-conduction path, which leads to the blowout port 18 from the ion electrodes 26 via the wall surface or the like of the duct case 17 having a supporting portion of the ion generating device 11, is prescribed a predetermined distance, for example, a length more than 100 mm in order to prevent a user or the like from getting an electric shock and secure safety. Since the electric-conduction distance is changed in accordance with voltage, if the voltage increases, the electric-conduction path for preventing the electric shock also becomes long.

Meanwhile, in the present embodiment, a shortest linear distance between the blowout port 18 and the ion electrodes 26 of the ion generating device 11 disposed in the vicinity of the blowout port 18 is set to the predetermined distance or less, for example, 100 mm or less in order to release a large amount of ions from the sanitary apparatus 6 including the hot air blower 10 with the ion generating device 11. An improved structure with respect to this point will be described with reference to FIGS. 8 to 10.

Figure 8:
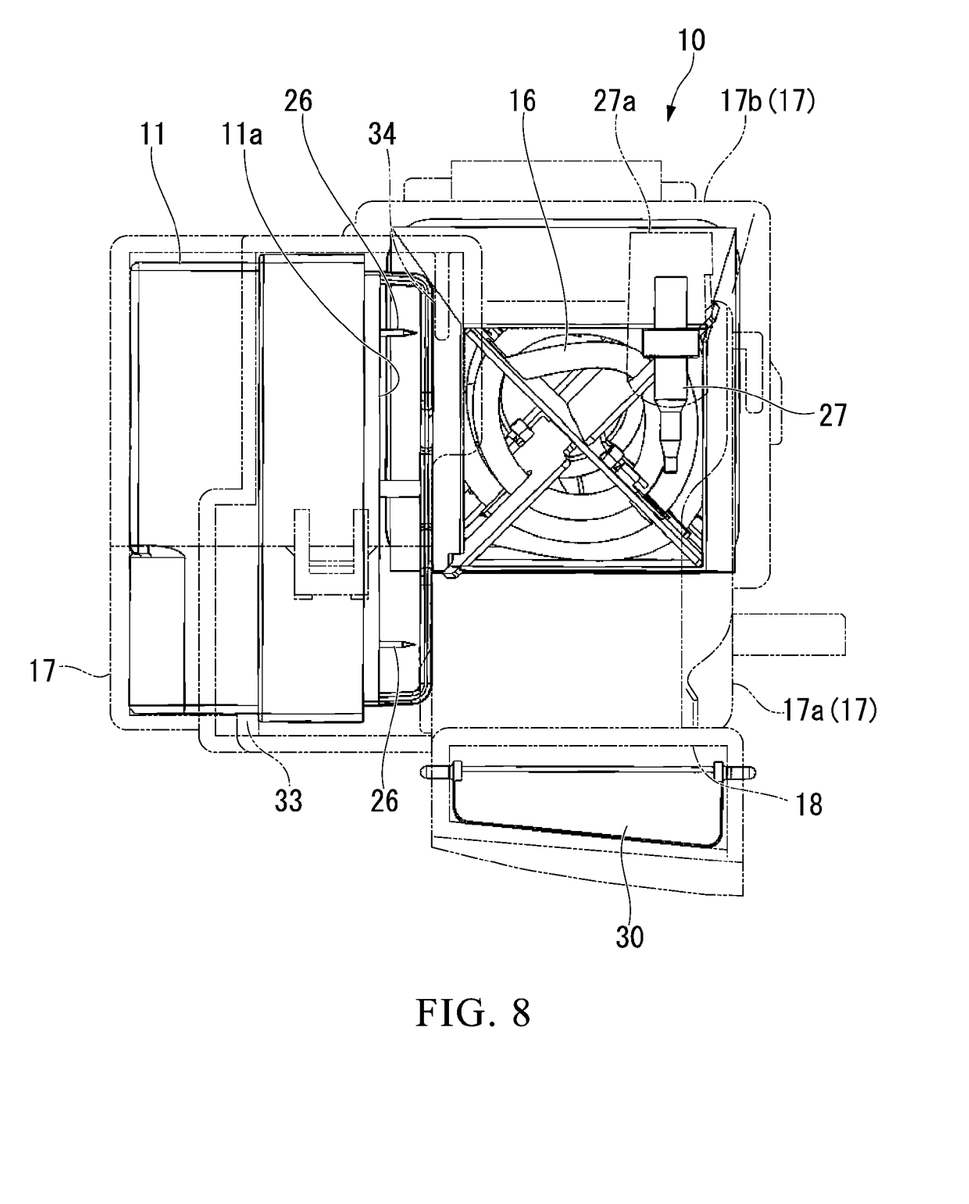
FIG. 8 is a view showing an upper support portion and a lower support portion in the duct case of the ion generating device of the present embodiment.

In the hot air blower 10 with the ion generating device 11, a duct case 17 which covers the air-blowing passage 20 along with the heater 16, the fan 15, the ion generating device 11, or the like is formed by fitting the lower duct case 17a with the upper duct case 17b. Moreover, as shown in FIG. 8, a lower portion of the ion generating device 11 is supported by a lower support portion 33 of the lower duct case 17a, and an upper side surface of the ion generating device 11 is supported by an upper support portion 34.

A gap of 1.5 mm or more is secured between the other outer peripheral surfaces of the ion generating device 11 and the duct case 17. By ensuring a gap of 1.5 mm or more, it is possible to prevent the current leaked from the ion electrodes 26 of the ion generating device 11 from being transmitted to the duct case 17.

Figure 9:
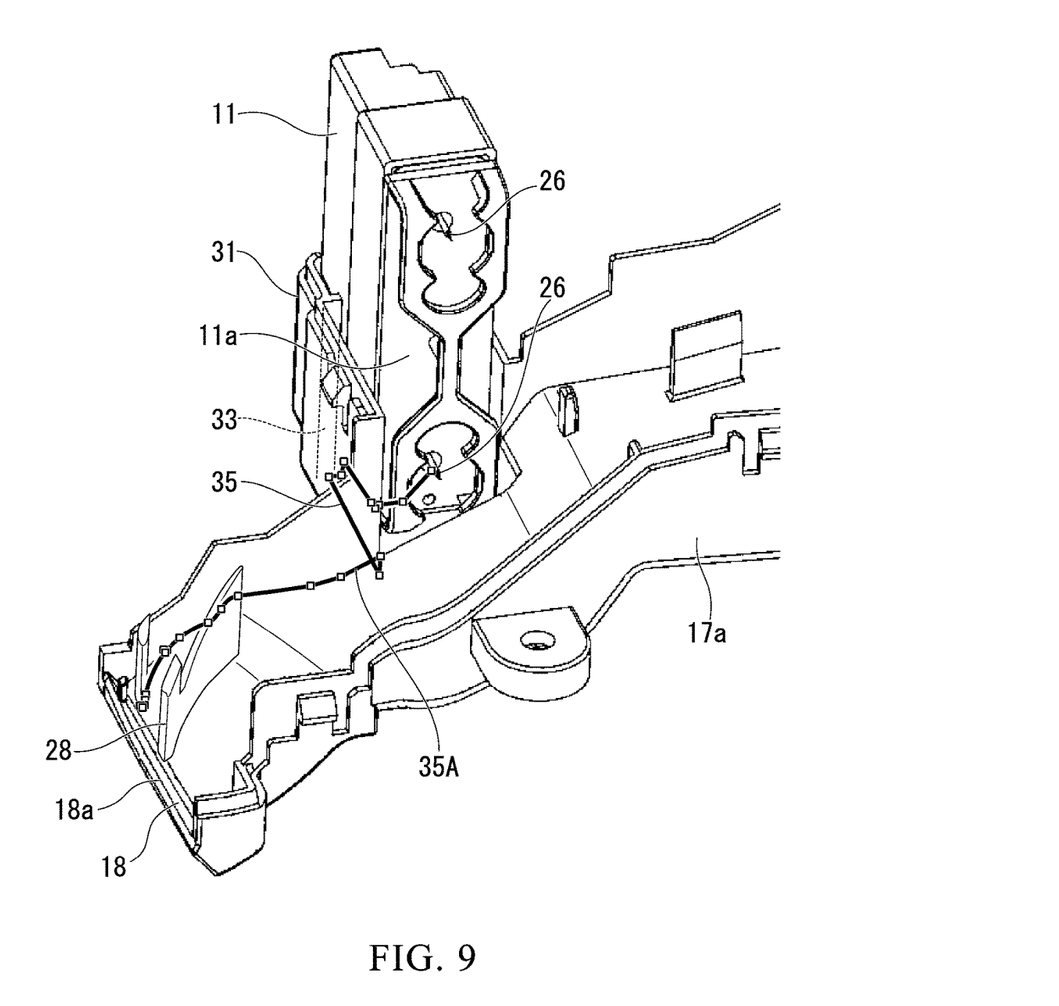
FIG. 9 is an explanatory view of a main portion showing a total distance of the ion generating device of the present embodiment along a wall surface between the lower support portion and the blowout port of a lower duct case.

In the lower duct case 17a shown in FIG. 9, the lower support portion 33 of the lower duct case 17a is connected to the lower portion of the ion generating device 11. FIG. 9 shows a lower transmission path 35A of current during the high-pressure discharge of the lower ion electrode 26. In the lower transmission path 35A, current flows from the ion electrodes 26 to the lower duct case 17a via the lower support portion 33, and flows to the blowout port 18 via a bypass path 35 on the wall surface of the lower duct case 17a while discharging the high-pressure by the lower ion electrode 26. Since the lower transmission path 35A is bent a plurality of times along the wall surface of the lower duct case 17a via the bypass path 35, for example, even when the linear distance from the lower support portion 33 to the blowout port 18 is close to 100 mm or less, the distance of the lower transmission path 35A along the wall surface of the lower duct case 17a is capable of being set to a length more than 100 mm.

Figure 10:
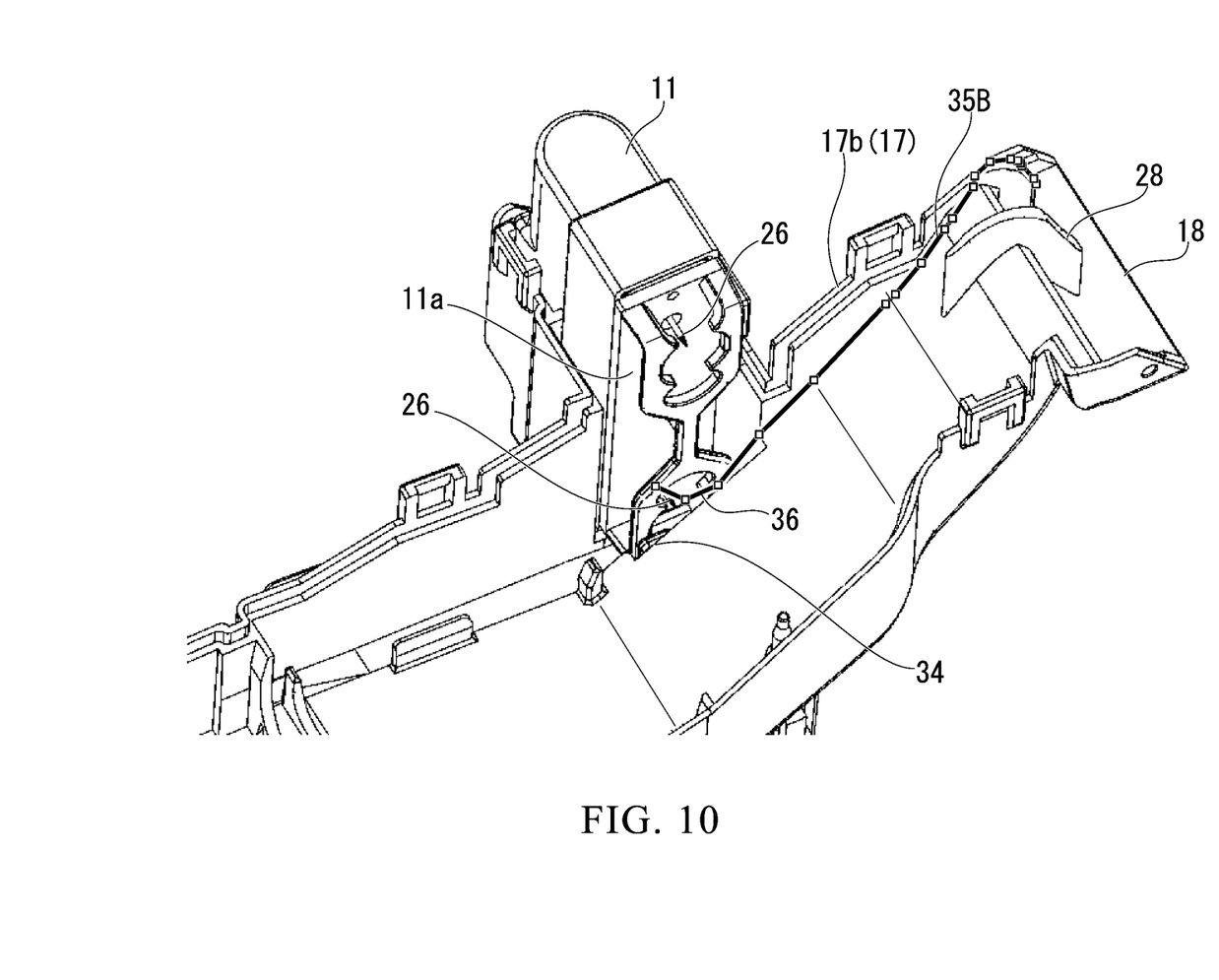
FIG. 10 is an explanatory view of a main portion showing the total distance of the ion generating device of the present embodiment along a wall surface between the upper support portion of the ion generating device and the blowout port of the upper duct case, and is an explanatory view of a main portion of the upper duct case and the ion generating device that are shown in a vertically inverted state.

Next, FIG. 10 is a view showing a state where the upper duct case 17b of the duct case 17 is inverted in the vertical direction, and indicates the upper electrode of the ion electrode 26 of the ion generating device 11.

Also in this case, an upper transmission path 35B of current during the high-pressure discharge of an upper ion electrode 26 is set. In the upper transmission path 35B, current flows from the upper ion electrode 26 to a wall surface of the upper duct case 17b via the upper support portion 34 and flows to the blowout port 18. For example, even if the linear distance from the upper support portion 34 to the blowout port 18 is close to 100 mm or less, since the upper transmission path passes through the bypass path 36, the distance of the upper transmission path 35B along the wall surface of the upper duct case 17b is capable of being set to be a length exceeding 100 mm.

Accordingly, in both of the lower support portion 33 and the upper support portion 34 that support the ion generating device 11, it is possible to prevent a user or the like from getting an electric shock at the blowout port 18 at the time of electric conduction so as to ensure safety, and it is possible to decrease the size of the sanitary apparatus 6. The supporting portion of the ion generating device 11 is not limited to the above-mentioned lower supporting portion 33 and the upper support portion 34, and a support portion is capable of being adopted at an appropriate position as long as the distance along the wall surface of the duct case 17 between the ion electrodes 26 and the blowout port 18 exceeds 100 mm.

The sanitary apparatus 6 according to the present embodiment has the above-described configuration, and the method of using the sanitary apparatus 6 will be mainly described with reference to FIGS. 5 and 6.

After using the flushing type toilet bawl 1, the fan 15, the heater 16 and the ion generating device 11 are operated. By driving the fan 15, most of air-blowing in amount is blown into the air-blowing tubular body 21 of the first air-blowing passage 22 as a main flow, and the remaining air-blowing is blown to the second air-blowing passage 23 as an auxiliary flow. In the first air-blowing passage 22, the air passes through the heater 16 in the air-blowing tubular body 21 to be heated, and the front end opening of the air-blowing tubular body 21 is tapered so that the opening becomes smaller than the rear end opening. Accordingly, the flow speed of the warm air which is the main flow flowing out from the front end opening increases. In addition, the blowing air does not hit the ion generating device 11.

Meanwhile, since the air blown through the second air-blowing passage 23 is widened from the rear end side to the front end side, the air is diffused. On the downstream side of the second air-blowing passage 23, the pair of ion electrodes 26 provided on the distal end surface 11a of the ion generating device 11 generates ions by high-pressure discharge. The ions are carried by the diffused air which is discharged from the second air-blowing passage 23. Since one side surface 21a of the second air-blowing passage 23 is inclined so as to be biased toward the first air-blowing passage 22 side toward the downstream side, ions are also diffused by the diffused auxiliary flow so as to be sent to the main flow side and joins the warm air in the junction portion 25 inside the duct case 17.

The joined warm air including the ions is guided to the local washing nozzle 9 side by the guide portion 28 in the duct case 17 and is directed to the blowout port 18. As shown in FIG. 6, the warm air is directed downward by the upper guide plate 29 in the duct case 17, and since the lower portion of the duct case 17 is closed by the lower guide 18a at the blowout port 18, the flow direction of the air blowing is changed toward the upper side.

Therefore, the warm air including ions is discharged diagonally upward from the blowout port 18. As a result, the local portion of the user after washing is capable of being warmed and dried, and the ions are discharged while being dispersed by air blowing, thereby sterilization and deodorization is capable of being performed.

The temperature of the warm air is measured by the thermistor 27 at the junction portion 25 on the downstream side of the first air-blowing passage 22 in the air-blowing passage 20, and the temperature is capable of being adjusted by performing a feedback the measurement result to the heater 16.

In the hot air blower 10 with the ion generating device 11 of the present embodiment, it is not necessarily necessary to discharge ions from the blowout port 18 in a state where the heater 16 is driven. For example, the ions may be discharged such that: air having the normal temperature is blew from the first air-blowing passage 22 as a main flow without driving the heater 16; the ions generated by the ion generating device 11 is diffused by using the air blowing from the second air-blowing passage 23 to join the ions with the main flow at the junction portion 25 of the air-blowing passage 20; and the ions are further diffused and discharged from the blowout port 18.

As described above, according to the sanitary apparatus 6 of the present embodiment, since the ion generating device 11 is installed on the downstream side from the heater 16, it is possible to generate the ions without being affected from the heat of the heater 16. In addition, since the ion generating device 11 is installed on the downstream side away from the first air-blowing passage 22, it is possible to decrease the heat influence of the warm air. Since the warm air passing through the heater 16 does not hit the ion generating device 11 due to the biased side surface 21a, the ion generating device 11 is not adversely affected by the heater 16 and the warm air.

According to the sanitary apparatus 6 of the present embodiment, since the first air-blowing passage 22 is formed in a tapered shape which narrows toward the blowout port 18 side, the flow speed of the warm air forming the main flow increases, the main flow allows to join the ions diffused at the auxiliary flow and is capable of effectively discharging the ions from the blowout port 18. As a result, it is possible to prevent the disappearance of ions before blowing out from the blowout port 18 and large amount of the ions are capable of discharging from the blowout port 18 to perform sterilization and deodorization.

Since the ion generating device 11 is capable of being installed on the downstream side from the heater 16 and are capable of being installed at the position at a position as close to the toilet bowl body 2 or the blowout port 18 as possible inside the front cover portion 5a of the cover 5 covering the function portion 4, it is possible prevent decreasing amount of ions before blowing out from the blowout port 18 and large amount of the ions are capable of efficiently discharging at the blowout port 18 and large amount of the ions are capable of effectively discharging from the blowout port 18.

The thermistor 27 which measures the temperature of the warm air having passed through the heater 16 is installed on the far side from the ion generating device 11 with respect to the center in the width direction of the junction portion 25 on the downstream side from the heater 16. Therefore, the thermistor 27 is less susceptible to heat from the heater 16 and the ion generating device 11.

For example, while the linear distance between the ion generating device 11 which performs high-pressure discharge using the ion electrodes 26 and the blowout port 18 is set to 100 mm or less, the lower transmission path 35A and the upper transmission path 35B along the wall surface of the duct case 17 from the ion electrodes 26 to the blowout port 18 via the lower support portion 33 and the upper support portion 34 pass through the bypass paths 35 and 36 and the extension lengths of the lower transmission path 35A and the upper transmission path 35B is capable of being set to the length exceeding 100 mm. As a result, many ions are capable of being discharged at the blowout port 18 and safety is capable of being secured.

Moreover, the hot air blower 10 with the ion generating device 11 or the sanitary apparatus 6 according to the present invention are not limited to the above-described embodiment, and appropriate modifications, replacements, or the like are capable of being be applied within a scope which does not depart from the gist of the present invention. Hereinafter, modifications or the like of the present invention will be described. The same reference numerals are used for components and members which are the same as or similar to the components and members described in the above embodiment, and descriptions thereof are omitted.

For example, in the above-described embodiment, as shown in FIG. 5, the heater 16 is installed inside the air-blowing tubular body 21 forming the first air-blowing passage 22, and the ion generating device 11 is installed on the downstream side away from the second air-blowing passage 23 arranged in parallel to the first air-blowing passage 22. However, the ion generating device 11 may be positioned at any location as long as the ion generating device 11 is installed on the downstream side from the heater 16, and for example, the ion electrodes 26 may be disposed inside the second air-blowing passage 23.

As shown in FIG. 6, in the vicinity of the blowout port 18 of the duct case 17, the upper guide plate 29 is provided on the upper surface of the duct case 17 and the lower guide 18a is formed in the blowout port 18. However, the present invention is not limited to this configuration. For example, instead of the upper guide plate 29 and the lower guide 18a, the lower duct case 17a may be formed to be inclined so as to gradually face upward toward the blowout port 18.

Moreover, a discharging angle of upward air discharged from the blowout port 18 is capable of being adjusted by an opening and closing angle of another shutter disposed outside of the shutter 30. For example, the upward air which is discharged from the blowout port 18 is capable of being set downward or the like.

In the present embodiment, the guide portion 28, which directs the warm air including ions to the local portion side, is provided in the vicinity of the blowout port 18 of the duct case 17. However, instead of this, the duct case 17 and the blowout port 18 may be formed so as to be bent or curved toward the local portion side.

In addition, in the first air-blowing passage 22 and the second air-blowing passage 23 in the air-blowing passage 20, the second air-blowing passage 23 may not necessarily be formed in a tapered shape which widens toward the front end side. For example, the side surface 21a of the air-blowing tubular body 21 on the second air-blowing passage side and the side wall 17c of the duct case 17 may be formed approximately parallel to each other. In short, the side surface 21a of the air-blowing tubular body 21 forming a partition wall in a plan view may be formed so as to be positioned biased toward the first air-blowing passage 22 side toward the front end side from the rear end side in order to disperse the ions and join the auxiliary flow with the main flow.

Moreover, the air-blowing tubular body 21 may not be installed in the first air-blowing passage 22, a partition wall such as the side surface 21a may be provided between the first air-blowing passage 22 and the second air-blowing passage 23. The partition wall need not be flat and may have any shape such as a curved plate shape or the like.

In addition, the first air-blowing passage 22 may not be formed in a tapered shape which narrows toward the front end side if the warm air does not hit the ion generating device 11, and the first air-blowing passage may have any shape for blowing air.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A sanitary apparatus, comprising:
   a fan for blowing air;
   an air-blowing passage which is provided on a downstream side from the fan and includes a first air-blowing passage and a second air-blowing passage which are partitioned from each other;
   a heater for heating air in the first air-blowing passage; and an ion generating device generating ions to be carried by the air blowing of the second air-blowing passage,
   wherein the ion generating device is installed on a downstream side from the heater so that the generated ions join the air blown from the first air-blowing passage by the air blowing of the second air-blowing passage,
   the ion generating device is installed downstream of a junction portion that joins the air blown from the first air-blowing passage with the air blowing from the second air-blowing passage, and
   a distal end surface of the ion generating device is disposed on an extension line of the second air blowing passage.

2. The sanitary apparatus according to claim 1, further comprising:
   a partition wall which faces the first air-blowing passage between the first air-blowing passage and the second air-blowing passage,
   wherein the partition wall is inclined gradually close to the first air-blowing passage side toward the downstream side of the air blowing.

3. The sanitary apparatus according to claim 1,
   wherein the second air-blowing passage is inclined gradually close to the first air-blowing passage side toward the downstream side of the air blowing.

4. The sanitary apparatus according to claim 1,
   wherein an upper guide portion and a lower guide portion are provided in the vicinity of a blowout port of the air-blowing passage in which the air blowing of the first air-blowing passage and the air blowing of the second air-blowing passage join with each other, and
   wherein the upper guide portion and the lower guide portion are formed such that the air blowing in the blowout port is directed upward by the upper guide portion and the lower guide portion.

5. The sanitary apparatus according to claim 1,
   wherein a temperature measuring device measuring a temperature of the air is installed in the air-blowing passage on the downstream side from the first air-blowing passage, and
   wherein the temperature measuring device is provided at a position that is opposed to a position at which the ion generating device is provided with respect to the center in a width direction of the air-blowing passage.

6. The sanitary apparatus according to claim 1, further comprising:
   a duct case covering the air-blowing passage and blowing out ions to be generated with the high-pressure discharge by an ion generating unit of the ion generating device from the blowout port of the air-blowing passage,
   wherein a linear distance between the ion generating unit of the ion generating device and the blowout port is set to a predetermined distance, and
   an electric-conductive distance is set to be longer than the predetermined distance by that a transmission path along a wall surface of the duct case between the ion generating unit and the blowout port which passes through a bypass portion in which the electric conduction is bypassed.

7. The sanitary apparatus according to claim 1, further comprising:
   a toilet bowl body; and
   a cover which covers the ion generating device,
   wherein the ion generating device is installed at a position inside and adjacent to a front cover portion of the cover, the front cover facing the toilet bowl body.

8. A sanitary apparatus, comprising:
   a fan for blowing air;
   an air-blowing passage which is provided on a downstream side from the fan and includes a first air-blowing passage and a second air-blowing passage which are partitioned from each other;
   a heater for heating air in the first air-blowing passage; and
   an ion generating device generating ions to be carried by the air blowing of the second air-blowing passage,
   wherein the ion generating device is installed on a downstream side from the heater so that the generated ions join the air blown from the first air-blowing passage by the air blowing of the second air-blowing passage,
   the ion generating device is installed downstream of a junction portion that joins the air blown form the first air-blowing passage with the air blowing from the second air-blowing passage, and
   a distal end surface of the ion generating device is disposed on a second air-blowing passage side.

* * * * *